United States Patent [19]

Ozai et al.

[11] Patent Number: 5,362,896
[45] Date of Patent: Nov. 8, 1994

[54] SILACYCLO RING COMPOUND HAVING ALKENOXY GROUPS

[75] Inventors: Toshiyuki Ozai; Masatoshi Arai, both of Gunma, Japan; Yoshifumi Inoue, Torrance, Calif.

[73] Assignee: Shin-Etsu Chemical Co., Inc., Tokyo, Japan

[21] Appl. No.: 224,468

[22] Filed: Apr. 7, 1994

[30] Foreign Application Priority Data

Apr. 7, 1993 [JP] Japan .................................. 5-105157

[51] Int. Cl.$^5$ .............................. C07F 7/08; C07F 7/18
[52] U.S. Cl. ...................................................... 556/464
[58] Field of Search .......................................... 556/464

[56] References Cited

U.S. PATENT DOCUMENTS

| | | | |
|---|---|---|---|
| 3,256,308 | 6/1966 | Sterling et al. | 556/464 |
| 3,337,598 | 8/1967 | Sterling et al. | 556/464 |
| 3,433,819 | 3/1969 | Braun | 556/464 |
| 5,099,052 | 3/1992 | Laine et al. | 556/464 X |
| 5,216,155 | 6/1993 | Laine et al. | 556/464 X |

*Primary Examiner*—Paul F. Shaver
*Attorney, Agent, or Firm*—Millen, White, Zelano & Branigan

[57] ABSTRACT

Organic silicone compounds characterized by the possession of a silacyclo ring, which is expressed by the following general formula:

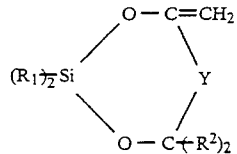

wherein R is a monovalent hydrocarbon group and Y is a divalent hydrocarbon group. These organic silicone compounds possess a high reactivity towards compounds having active hydrogens, especially alcohols. Therefore, they are extremely useful as silylation agents, surface treatment agents and adhesion promoters.

8 Claims, No Drawings

SILACYCLO RING COMPOUND HAVING ALKENOXY GROUPS

This invention relates to novel organic silicone compounds, particularly to silacyclo ring compounds having alkenoxy groups.

BACKGROUND OF THE INVENTION

Conventionally variously types of organic silicone compounds have been utilized as silylation agents, surface treatment agents, and adhesion promoters on substances in order to improve their physical properties.

The organic silicone compounds utilized for these applications must have a high reactivity towards the substances which are treated to improve their physical properties. The purpose of this invention is to provide novel organic silcone compounds which have a high reactivity and which are also useful as silylation agents, surface treatment agents, and adhesion promoters.

SUMMARY OF THE INVENTION

The invention provides a silacyclo ring compound which is expressed by the following general formula (1):

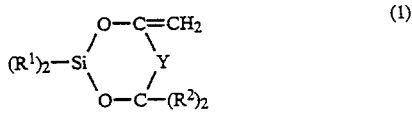 (1)

wherein $R^1$ is either a hydrogen atom, or an unsubstituted or substituted monovalent hydrocarbon group, preferably of 1 to 8 carbon atoms, each $R^1$ group may be the same or different; $R^2$ is either a hydrogen atom, or a unsubstituted or substituted monovalent hydrocarbon group, preferably of 1 to 8 carbon atoms, each $R^2$ group may be the same or different; and Y is a bivalent hydrocarbon group, preferably of 1 to 6 carbon atoms or both $R^2$ groups together may be a substituted or unsubstituted, branched or linear, monovalent hydrocarbon group, preferably of 1 to 8 carbon atoms, double bonded to the silacyclo ring.

Further, the invention provides a silacyclo ring compound which is expressed by the following general formula (2):

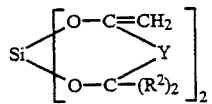 (2)

wherein $R^2$ and Y are the same groups as described above.

Upon further study of the specification and appended claims, further objects and advantages of this invention will become apparent to those skilled in the art.

The organic silicone compounds of this invention, which are expressed by these general formulae (1) or (2), possess the Si—O—C=CH$_2$ (alkenoxy group) as well as a cyclic structure. As a result, they possess an extremely high reactivity towards compounds having active hydrogens, such as, for example, alcohols.

For example, these compounds react with alcohols by the following equation:

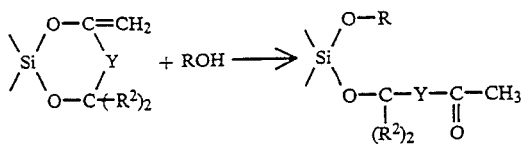

wherein R is a monovalent hydrocarbon group, such as, for example, an alkyl group and $R^2$ and Y are the same as described above. Therefore, the compounds of the invention are extremely useful as silylation agents, surface treatment agents and adhesion promoters. For example, the compounds are useful as silylation agents to alcohols, such as, e.g., isopropyl alcohol, methyl alcohol and ethyl alcohol; amines, such as, e.g., ammonia, diethylamine and n-butylamine; and mercapto compounds, such as, e.g., ethylthiol and butylthio. They are particularly useful as silylation agents for alcohols. Further, for example, the compounds are useful as primers for adhesion promotion between, e.g., fluorocarbon resins and silicone elastomers when used together with titanium alkoxides and solvents, for example.

In the above general formula (1), $R^1$ is either a hydrogen atom or an unsubstituted or substituted, branched or linear, monovalent hydrocarbon group, preferably of 1 to 8 carbon atoms and preferably an aliphatic group. Examples of such monovalent hydrocarbon groups are: alkyl groups such as a methyl group, an ethyl group, and a butyl group; alkenyl groups of 2 to 8 carbon atoms such as a vinyl group; and said groups where at least part of the hydrogen atoms are substituted by halogen atoms, such as a chloromethyl group and a 3,3,3-trifluoropropyl group.

In the formulae (1) and (2), $R^2$ is either a hydrogen atom or an unsubstituted or substituted, branched or linear monovalent hydrocarbon group, preferably of 1 to 8 carbon atoms, or both $R^2$ groups together may be a substituted or unsubstituted, branched or linear, monovalent hydrocarbon group, preferably of 1 to 8 carbon atoms, double bonded to the silacyclo ring. Examples of such monovalent hydrocarbon groups are the same as described for $R^1$ above.

Further, Y is a bivalent hydrocarbon group, preferably of 1 to 6 carbon atoms. Examples thereof are linear or branched chain alkylene groups. Alkylene groups of 1 or 2 carbon atoms are particularly preferred.

Representative of organic silicone compounds expressed by the general formula (1) are listed below. In the following formulae, Me, Et, Pr, Vi and Ph designate a methyl group, an ethyl group, a propyl group, a vinyl group, and a phenyl group, respectively. (These designations are the same throughout the specification).

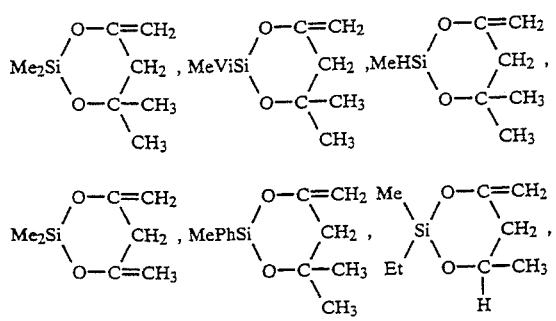

-continued

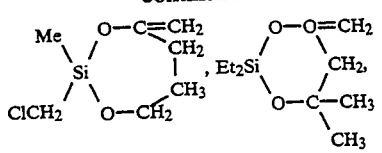

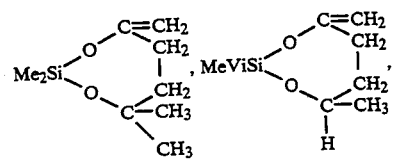

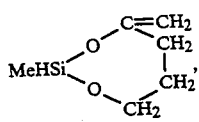

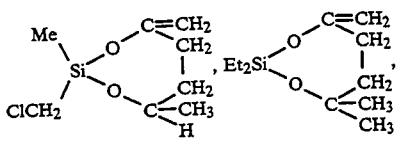

The organic silicone compounds expressed by the general formula (1) possess one silacyclo ring, while the organic silicone compounds expressed by the general formula (2) possess two silacyclo rings. In general formula (2), $R^2$ and Y are the same groups as described above and appropriate examples thereof include those shown for $R^1$. Representative of the organic silicone compounds expressed by the general formula (2) are those listed below:

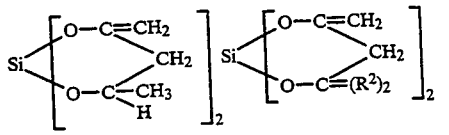

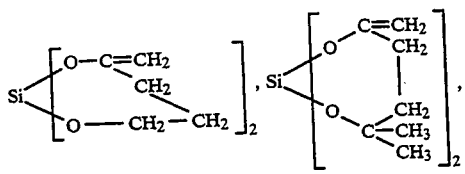

The organic silicone compounds of this invention possess a high reactivity towards compounds having active hydrogens, especially alcohols, therefore they are extremely useful as silylation agents, surface treatment agents, for example, for silica, and adhesion promoters.

The organic silicone compounds of this invention are readily synthesized by the reaction of, for example, the compounds expressed by the general formula (3) below:

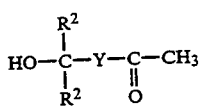

(3)

or the compounds expressed by the general formula (4) below:

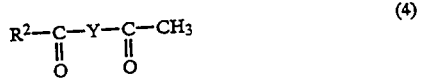

(4)

with dichlorosilane or tetrachlorosilane through a condensation cyclization. For example, utilization of dichlorosilane results in the organic silicone compounds expressed by the general formula (1) and the utilization of tetrachlorosilane results in the organic silicone compounds expressed by the general formula (2).

It is desirable to carry out the condensation cyclization reaction using an alkali catalyst. The appropriate reaction temperature is, in general, from 10° to 150° C. and an appropriate inert solvent is employed for the reaction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Japanese No. 5-105,157, filed Apr. 7, 1993, are hereby incorporated by reference.

EXAMPLES

Example 1

116.2 g of 4-hydroxy-4-methyl-2-pentanone (1 tool), 202.4 g of triethyl amine (2 mol), and 100 g of hexane were placed in a two liter capacity four neck flask equipped with a stirrer, a condenser, a thermometer, and a dropping funnel and stirred for 30 minutes at room temperature. Then 142.2 g of dichloromethyl vinyl silane (1 mol) was added drop by drop while stirring in an ice bath, and then 100 g of hexane was further added. This drop-by-drop addition took 30 minutes. Then the mixture was further stirred at room temperature until the gas chromatographic peak of triethyl amine disappeared. After completion of the reaction, the precipitated triethyl amine hydrochloride was removed through filtration and the reaction mixture was condensed. Distillation under reduced pressure (boiling point 61° C. at 23 mmHg) recovered 147.24 g of the compound (1) at 80% yield.

The analytical results of this compound are listed below:

| MS Analysis | |
|---|---|
| m/e: | 184 |
| NMR Analysis | |
| δ (ppm) | |
| 0.14 | (s, 3H, Si—CH$_3$) |
| 1.24 | (s, 6H, C—CH$_3$) |
| 1.74 | (s, 1H, CH$_2$=C) |
| 2.08 | (s, 1H, CH$_2$=C) |
| 1.80–2.10 | (broad, 3H, CH$_2$=CH—Si) |
| 5.4 | (s, 2H, —CH$_2$—) |

The structure of the compound (1), identified by the above analytical results, is shown below along with its synthetic reaction equation.

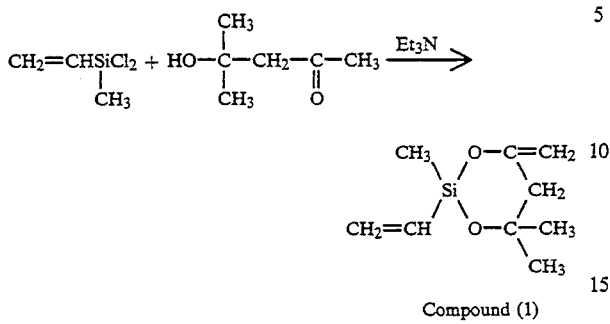

Compound (1)

Example 2

100.1 g of 2,4-pentadione (1 mol), 202.4 g of triethyl amine (2 mol), and 100 g of hexane were placed in similar equipment as described in Example 1 and stirred for 30 minutes at room temperature. Then 129.1 g of dichlorodimethyl silane (1 mol) was added drop by drop while stirring in an ice bath, and then 100 g of hexane was further added. This drop-by-drop addition took 30 minutes. Then the mixture was further stirred at room temperature until the gas chromatographic peak of triethyl amine disappeared. After the completion of the reaction, the precipitated triethyl amine hydrochloride was removed through filtration and the reaction mixture was condensed. Distillation under reduced pressure (boiling point from 79° to 81° C. at 69 to 70 mmHg) recovered 129.1 g of the compound (2) at 82% yield.

The analytical results of this compound are listed below.

| MS Analysis | |
|---|---|
| m/e: | 156 |
| NMR Analysis | |
| δ (ppm) | |
| 0.13 | (s, 6H, Si—CH$_3$) |
| 1.06 | (s, 2H, CH$_2$=C) |
| 2.20 | (s, 2H, CH$_2$=C) |
| 5.80 | (s, 2H, —CH$_2$—) |

The structure of the compound (2), identified by the above analytical results, is shown below along with its synthetic reaction equation.

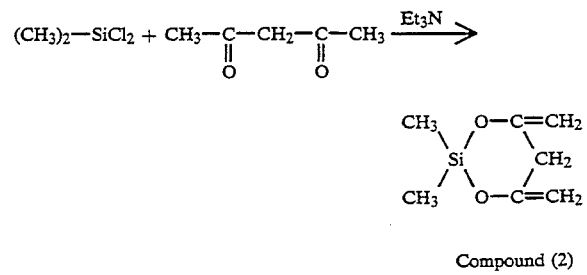

Compound (2)

Example 3

232.4 g of 4-hydroxy-4-methyl-2-pentanone (2 mol), 404.8 g of triethyl amine (4.1 mol), and 100 g of hexane were placed in similar equipment as described in Example 1 and stirred for 30 minutes at room temperature.

Then 170.1 g of tetrachlorosilane (1 mol) was added drop by drop while stirring in an ice bath, and then 100 g of hexane was further added. This drop-by-drop addition took 40 minutes. Then the mixture was further stirred at room temperature until the gas chromatographic peak of triethyl amine disappeared and this reaction mixture was further aged at 60° C. for two hours. After the completion of the reaction, the precipitated triethyl amine hydrochloride was removed through filtration and the reaction mixture was condensed. Distillation under reduced pressure (boiling point from 110° to 113° C. at 13 mmHg) recovered 179.2 g of the compound (3) at 70% yield.

The analytical results of this compound are listed below.

| MS Analysis | |
|---|---|
| m/e: | 256 |
| NMR Analysis | |
| δ (ppm) | |
| 1.54 | (s, 6H, C—CH$_3$) |
| 2.53 | (s, 2H, —CH$_2$—) |
| 4.19 | (s, 1H, CH$_2$=C) |
| 4.55 | (s, 1H, CH$_2$=C) |

The structure of the compound (3), identified by the above analytical results, is shown below along with its synthetic reaction equation.

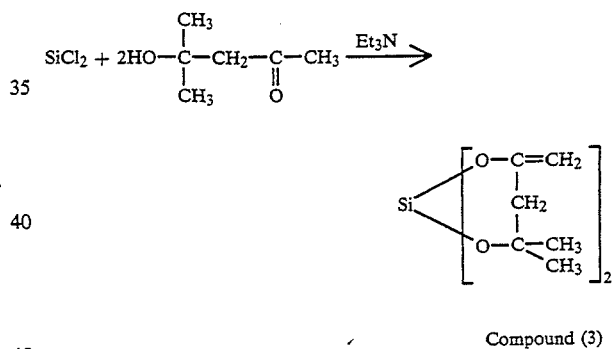

Compound (3)

Application Example 1

1.85 g of the compound 1 obtained in Example 1 and 7.5 g of isopropyl alcohol were placed in a 50 ml capacity Erlenmeyer flask equipped with a stirrer and a magnetic stirrer, along with 1.8 g of n-decane as an internal reference. The reaction between the compound (1) and isopropyl alcohol was traced by the method of gas chromatography. After 30 minutes, the compound (1) completely reacted with isopropyl alcohol and produced a reaction product (1). The reaction scheme is shown below.

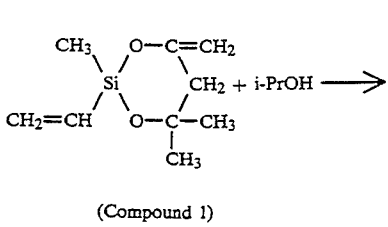

(Compound 1)

-continued

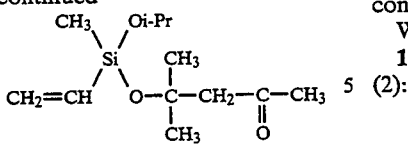

Reaction Product (1)

Application Example 2

1.56 g of compound (1) obtained from Example 1 and 7.3 g of diethylamine were added into a 50 ml-flask having a magnetic stirrer.

Further, 1.8 g of n-decane was added thereto as a standardizing solution and the reaction of compound (1) and diethylamine was traced by gas chromatography.

After 30 minutes, reaction product (2) was prepared by reaction of compound (1) and diethylamine above. This reaction is as follows:

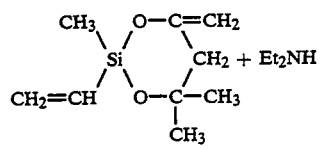

(Compound 1)

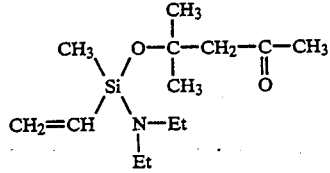

Reaction Product (2)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A silacyclo ring compound of the formulae (1) or (2):

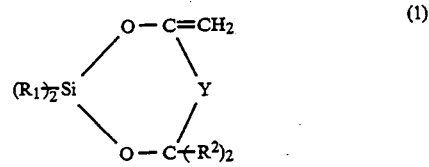

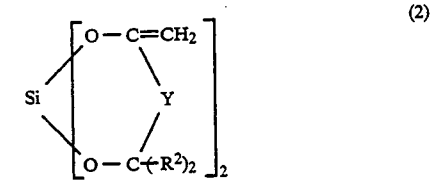

wherein $R^1$ is either a hydrogen atom, or an unsubstituted or substituted, branched or unbranched, monovalent hydrocarbon group of 1 to 8 carbon atoms, each $R^1$ being the same or different; $R^2$ is either a hydrogen atom, or an unsubstituted or substituted, branched or unbranched, monovalent hydrocarbon group of 1 to 8 carbon atoms, each $R^2$ being the same or different or both $R^2$ groups together may be an unsubstituted or substituted, branched or linear, monovalent hydrocarbon group of 1 to 8 carbon atoms, double bonded to the silacyclo ring; and Y is a bivalent branched or linear hydrocarbon group of 1 to 6 carbon atoms.

2. The compound of claim 1, wherein $R^1$ and each $R^2$ are independently an alkyl of 1 to 8 carbon atoms or alkenyl group of 2 to 8 carbon atoms, optionally substituted by halogen atoms.

3. The compound of claim 1, wherein $R^1$ and each $R^2$ are independently a methyl, ethyl, butyl, vinyl, chloromethyl or 3,3,3-trifluoropropyl group.

4. The compound of claim 1, wherein Y is an alkylene group of 1 to 6 carbon atoms.

5. The compound of claim 1, wherein Y is an alkylene group of 1 or 2 carbon atoms.

6. The compound of claim 1 of the formula (1).

7. The compound of claim 1 of the formula (2).

8. The compound of claim 1, wherein both $R^2$ groups together form a group double bonded to the silacyclo ring.

* * * * *